United States Patent [19]

Kaila et al.

[11] 4,353,914
[45] Oct. 12, 1982

[54] ANTITUSSIVE ANILIDES

[75] Inventors: Juhani O. W. Kaila; Erkki J. Honkanen; Joachim E. Alberty; Jaakko J. Hukki, all of Helsinki, Finland

[73] Assignee: Orion-yhtyma Oy, Finland

[21] Appl. No.: 111,508

[22] Filed: Jan. 11, 1980

Related U.S. Application Data

[62] Division of Ser. No. 7,170, Jan. 29, 1979, abandoned.

[30] Foreign Application Priority Data

Feb. 7, 1978 [FI] Finland ................................ 780387

[51] Int. Cl.³ ................ A61K 31/165; A61K 31/445
[52] U.S. Cl. .................................... 424/267; 424/324
[58] Field of Search ................................ 424/267, 324

[56] References Cited

U.S. PATENT DOCUMENTS 2,904,586  9/1959  Ruschig et al. ..................... 260/500
3,542,850  11/1970  Jansen et al. ....................... 260/471
4,125,730  11/1978  Hidaka et al. ....................... 560/37

FOREIGN PATENT DOCUMENTS 634073  3/1950  United Kingdom .
760023  10/1956  United Kingdom .
809286  2/1959  United Kingdom .

OTHER PUBLICATIONS

Foye-"Principles of Medicinal Chemistry", (Textbook), pp. 312-315, 804-808 (1976).

Primary Examiner—Leonard Schenkman
Attorney, Agent, or Firm—Biebel, French & Nauman

[57] ABSTRACT

The invention relates to novel antitussive anilides and non-toxic acid addition salts thereof. These novel compounds have the general formula

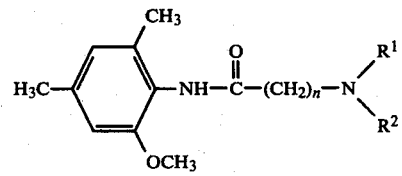

wherein n is an integer from 2 to 3, and substituents $R^1$ and $R^2$ are lower alkyl groups or form together with the nitrogen atom to which they are attached a piperidine ring which is substituted by a methyl group. The invention also relates to a process for preparing these novel compounds.

2 Claims, No Drawings

ANTITUSSIVE ANILIDES

This is a division of application Ser. No. 7,170 filed Jan. 29, 1979, now abandoned.

BACKGROUND OF THE INVENTION

It is known that the actual central cough-relieving action of antitussives can be increased by their simultaneous peripheral local anesthetic effect. Such antitussives of the local anesthetic type include anesthesin (p-aminobenzoic acid ethyl ester) and benzonatate (p-butylaminobenzoic acid w-O-methyleneglycol ester).

SUMMARY OF THE INVENTION

The object of the present invention is to produce novel antitussive compounds of the local anesthetic type; they are distinguished from the above antitussives of the ester type in that they are anilides. The compounds according to the invention have the following general formula:

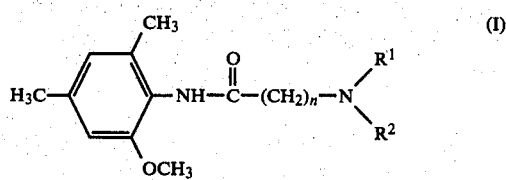

where n is an integer from 2 to 3 and substituents $R^1$ and $R^2$ each separately represent a lower alkyl group having 1 to 3 carbon atoms, or together with the nitrogen atom they form a heterocyclic ring.

In addition to free bases in accordance with the above general formula (I) the scope of the invention also covers their nontoxic acid addition salts.

The compounds according to the invention are prepared by a method known per se by acylating 4,6-dimethyl-o-anisidine

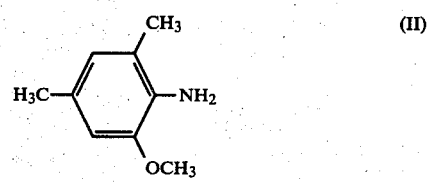

with a halogen-carboxylic acid halide of the general formula:

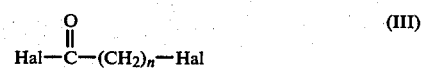

wherein Hal is chlorine or bromine and n the same as above, and by reacting the resultant halogen-carboxylic acid anilide of the general formula

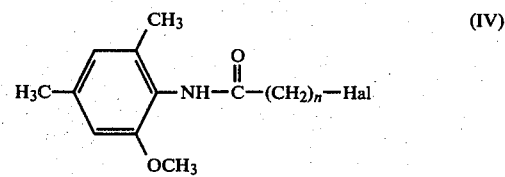

wherein n and Hal are as defined above, with an amine having the general formula:

wherein $R^1$ and $R^2$ are as defined above.

In the reaction between the halogen-carboxylic acid anilide (IV) and the amine (V) it is advantageous to use the latter in excess in order to bind the hydrogen halide released in the reaction. In this case it is also possible to perform the reaction without a solvent. Temperatures up to 120° may be used. If desired, ethanol, benzene or xylene, for example, can be used as a solvent. The reaction product is a basic anilide (I), which as such can be isolated and purified. It is, however, more advantageous to convert it directly to hydrochloride by means of hydrogen chloride gas. The hydrochloride may also, if desired, be easily converted to the free base in purified form by treating it with sodium carbonate.

It is preferable to perform the acylation of 4,6-dimethyl-o-aniside (II) with halogen-carboxylic acid halide (III) in a buffer solution of acetic acid and sodium acetate, using starting substances II and III in approximately equimolecular proportions.

The 4,6-dimethyl-o-anisidine (II) used as starting material can be prepared from 3,5-dimethyl phenol in a manner known from the literature (Auwers and Borsche, Ber. 48, 1698–1716 (1915)).

The compounds according to the invention are novel compounds, which are characterized not only by their local anesthetic activity but also by their strong antitussive activity. This is shown in that, when administrated intravenously or orally, they stop or relieve coughing which has been produced by electric irritation of nervus laryngeus sup. in a cat under anesthesia or by adding ammonia spray to the air breathed in by a guinea pig not under anesthesia.

There are well-known anilides and xylidides of amino acids which have been used parenterally as local anesthetics. The best known of them is lidocaine or 2-diethylamino-2',6'-acetoxy-xylidide. These known compounds differ from the compounds of the present invention principally regarding the substitution of the aromatic group, but partly also regarding the amino acid portion. These known products have not been proven to have any antitussive activity except the cough reflex suppressant activity of lidocaine when used intravenously, (J. Steinhaus and L. Gaskin, Anesthesiology 1963, 24, 285–90). In regard to the use as an antitussive this has, however, no significance since lidocain is not suitable for oral use.

Regarding the antitussive activity the compounds of the invention show, especially when administered orally, a strong activity.

When tested according to Domenjoz's method (Naunyn-Schmiedebergs' Arch. exp. Pathol. Pharmacol. 1952, Vol. 215, p. 18) the activity of the compounds according to examples 1 to 3 at electric irritation of nervus laryngeous sup. in an anesthesized cat, when administrated intravenously, was clear but weaker than with codeine phosphate.

At inhalation of ammonia in an anesthesized guinea pig (Källqvist & Melander, Arzneimittelforschung 1957, 7, 301–304) 10 mg/kg of the compound of example 1, administrated orally, was more effective than 15 mg/kg of codeine phosphate. 20 mg/kg of the compound of example 2 was remarkably more effective than 15 mg/kg of codeine phosphate, whereas already 2.5 mg/kg of the compound of example 3 was more effective than 15 mg/kg of codeine phosphate.

At inhalation of sulphur dioxide in an anesthesized guinea pig a dose of 20 mg/kg of the compound of example 1, orally administrated, was more effective than 5 mg/kg of codeine phosphate and 20 mg/kg of the compound of example 2 more effective than 15 mg/kg of codeine phosphate, whereas a dose of 2.5 mg/kg of the compound of example 3 was sufficient for bringing forth a more effective activity than with 5 mg/kg of codeine phosphate.

The local anesthetic activity of the compound of example 1 is with infiltration anesthesia about 1.6 and with conduction anesthesia about 1.4 times stronger than that of lidocaine and by the compound of example 2 correspondingly 1.6 and 3 times stronger, whereas the corresponding values of the compound of example 3 are 4 and 1.8 times those of lidocaine.

The acute toxicity $LD_{50}$ of the compound of example 1 in a mouse by oral administration is of the same order as those of codeine and lidocaine. The corresponding value of the compound of example 2 is somewhat greater and of the compound of example 3 respectively somewhat smaller than those of the reference compounds.

DESCRIPTION OF THE PREFERRED EMBODIMENTS

The invention is illustrated by the following examples:

EXAMPLE 1

(a) 4-Chloro-4',6'-dimethyl-o-butyranisidide

A quantity of 113 g (0.8 mol) of 4-chloro-buturyl chloride was added, while cooling and vigorously stirring, to a solution of 110 g (0.73 mol) of 4,6-dimethyl-o-anisidine (Auwers and Borsche, Ber. 48, 1698–1716 (1915)) in 340 ml of glacial acetic acid. The resultant solution was added, while stirring, to another solution of 222 g of crystalline sodium acetate in 665 ml of water. Stirring was continued for 1 h at room temperature. The precipitate formed was filtered, washed well with water, and dried. The yield was 135.8 g (72.8%). Upon crystallization from benzene the melting point 108°–110° C. was obtained.

$C_{13}H_{18}ClNO_2$: Calc. Cl 13.85; N 5.47. Obs. Cl 13.52; N 5.57.

(b) 4-(Diethylamino)-4',6'-dimethyl-o-butyranisidide

A mixture of 61.8 g (0.24 mol) of 4-chloro-4',6'-dimethyl-o-butyranisidide, 360 ml of diethylamine and 1 g of potassium iodide was heated for 48 h at 65° C. The excess diethyl amine was distilled off, and water and sodium carbonate (25 g) were added to the residue. The mixture was extracted with dichloromethane. The extract was evaporated to dryness, the residue was dissolved in anhydrous acetone and saturated with HCl gas. The product thereby precipitated as hydrochloride, which was filtered and washed with anhydrous acetone. The yield was 52.7 g (66%). By crystallizing the raw product from isopropanol, 50.0 g (62%) of pure hydrochloride was obtained, m.p. 185°–186° C.

$C_{17}H_{28}N_2O_2$ x HCl: Calc. C 62.08; H 8.88; N 8.51. Obs. C 62.45; H 8.62; N 8.39.

When a free base was desired instead of the hydrochloride, the latter was treated with a soda solution. The released base was extracted with dichloromethane, the solution was dried with potassium carbonate and filtered, and the solvent was removed by evaporation. Upon crystallization of the residue from petroleum ether (b.p. 40° C.) to which some benzene had been added, a free base was obtained, m.p. 92°–93° C.

$C_{17}H_{28}N_2O_2$: Calc. C 69.82; H 9.65; N 9.58. Obs. C 70.07; H 9.19; N 9.76.

EXAMPLE 2

(a) 3-Chloro-4',6'-dimethyl-o-propionanisidide

By using 92.8 g (0.615 mol) of 4,6-dimethyl-o-anisidine and 86 g (0.68 mol) of 3-chloropropionyl chloride as starting compounds, 115.3 g (77.4%) of 3-chloro-4',6'-dimethyl-o-propionanisidide, m.p. 123°–125° C. (crystallized from benzene) was obtained by the procedure described in Example 1a).

(b) 3-(Dipropylamino)-4',6'-dimethyl-o-propionanisidide

A mixture containing 50 g (0.206 mol) of 3-chloro-4',6'-dimethyl-o-propionanisidide, 310 ml of di-n-propylamine, and 1 g of potassium iodide was heated for 48 h at 110° C. 57.7 g (81.4%) of hydrochloride of the raw product was obtained by treating the reaction mixture by the procedure described in Example 1b). Upon crystallization from isopropanol, 48 g (67.5%) of pure hydrochloride was obtained, m.p. 174° C.

$C_{18}H_{30}N_2O_2$ x HCl: Calc. C 63.03; H 9.11; N 8.17. Obs. C 63.41; H 8.95; N 8.28.

EXAMPLE 3

3-(2-Methylpiperidyl)4',6'-dimethyl-o-propionanisidide

A mixture containing 40 g (0.165 mol) of 3-chloro-4',6'-dimethyl-o-propionanisidide, prepared by the procedure described in Example 2a), 54.3 g of 3-methyl piperidine, and 330 ml of anhydrous benzene was heated for 72 h at 65° C. 47.7 g (84.5%) of hydrochloride of 3-(2-methyl piperidyl)-4',6'-dimethyl-o-propionanisidide was obtained by treating the reaction mixture by the procedure described in Example 1b). 32.1 g/57%) of pure hydrochloride was obtained, m.p. 192°–193° C., upon crystallization of the raw product from a mixture of isopropanol and acetone.

The hydrochloride obtained above was converted to the free base, m.p. 77°–78° C., by the procedure described in Example 1.

$C_{18}H_{28}N_2O_2$: Calc. C 71.01; H 9.27; N 9.20. Obs. C 70.70; H 8.94; N 9.23.

What is claimed is:

1. A process for relieving coughing comprising administering to a subject an effective amount of a compound having the general formula

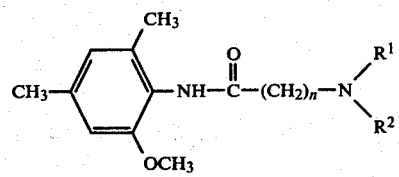

wherein n is an integer from 2 to 3, and $R^1$ and $R^2$ each separately represent a lower alkyl group having 1 to 3 carbon atoms, or they form together with the nitrogen atom to which they are attached a piperidine ring which is substituted by a methyl group, and non-toxic acid addition salts thereof.

2. The process of claim 1 in which the compound is administered orally.

* * * * *